United States Patent [19]
Verny

[11] Patent Number: 5,082,665
[45] Date of Patent: Jan. 21, 1992

[54] ANTI-SNORING FORMULATIONS USING YOHIMBINE

[75] Inventor: Tom Verny, 36 Madison Ave., Toronto, Ontario, Canada, M5R 2S1

[73] Assignees: Tom Verny, Toronto; Ivor M. Hughes, Markham, both of Canada

[21] Appl. No.: 493,763

[22] Filed: Mar. 15, 1990

[51] Int. Cl.⁵ .......................... A61K 31/40; A61K 9/20
[52] U.S. Cl. .................................... 424/464; 424/484; 514/923
[58] Field of Search .......................... 424/464; 514/923

[56] References Cited
U.S. PATENT DOCUMENTS

| | | | |
|---|---|---|---|
| 3,940,387 | 2/1976 | Saint-Ruf et al. | 546/53 |
| 4,310,524 | 1/1982 | Wiech et al. | 514/646 |
| 4,876,283 | 10/1989 | Reichert | 514/923 |

Primary Examiner—Thurman K. Page
Assistant Examiner—Edward J. Webman
Attorney, Agent, or Firm—Ivor M. Hughes

[57] ABSTRACT

A formulation for use to treat a person who snores when he or she sleeps, the said formulation comprising an effective amount of yohimbine ($3\alpha$-$15\alpha$-$20\beta$-$17\alpha$-hydroxy yohimbine-$16\alpha$carboxylic acid methyl ester) and pharmaceutically tolerable forms thereof (for example, salts, esters and the like), in a pharmaceutically acceptable carrier.

2 Claims, No Drawings

ANTI-SNORING FORMULATIONS USING YOHIMBINE

FIELD OF INVENTION

This invention relates to formulations suitable for treating snoring.

BACKGROUND OF THE INVENTION

Snoring is a very serious problem, not only for the individuals but also with the partner with whom such individual sleeps.

It is therefor an object of this invention to provide formulations suitable for use to treat persons who snore when they sleep and a method of treating such a person who snores when sleeping.

Further and other objects of the invention will be realized by those skilled in the art from the following summary of the invention and detailed description thereof.

SUMMARY OF THE INVENTION

According to one aspect of the invention a formulation is provided for use to treat a person who snores when he or she sleeps, the said formulation comprising an effective amount of yohimbine (3α-15α-20β-17α-hydroxy yohimbine-16α-carboxylic acid methyl ester) and pharmaceutically tolerable forms thereof (for example, salts, esters, and the like), in a pharmaceutically acceptable carrier to inhibit snoring in persons who snore. One formulation may comprise a compressed tablet which contains (1/12 gr.) 5.4 mg of yohimbine hydrochloride in a pharmaceutically tolerable carrier. This formulation may be taken by the person suffering from snoring before bedtime.

According to another aspect of the invention an improved treatment for a person who snores may comprise the administration to the patient, an effective, amount of the yohimbine or any pharmaceutically tolerable form thereof (for example, salts thereof [e.g. hydrochloride], esters, and the like) in a pharmaceutically tolerable carrier for the treatment of snoring for inhibiting snoring in persons who snore. Such process may, for example, comprise the administration of one tablet of (1/12 grain) 5.4 mg of yohimbine hy 'rochloride before bedtime.

One source of the yohimbine is found in a preparation Yocon (T.M.) manufactured by Palisades Pharmaceuticals Inc., Tenafly, New Jersey U.S.A 07670. A distributor of the Yocon (T.M.) is Glenwood Laboratories Canada Limited, Mississauga, Ontario, L5T 1H3.

Yohimbine is described in the literature [the Product monograph of Palisades Pharmaceuticals, Inc., Tenafly, N.J. and "Effect of Yohimbine Hydrochloride On Erectile Impotence: A Double-Blind Study" *The Journal of Urology* Vol. 141, June 1989 at page 1360] as an alpha adrenergic blocking agent having contraindications of renal or hepatic insufficiency. The user of the drug, according to the product monograph provided by the manufacturers of Yocon (T.M.) is warned under precautions that "Yohimbine may injure kidneys and cause hypotension. The possibility of a fatal overdose of yohimbine when associated with ingestion of alcohol must be considered. An overdose treatment is provided as follows:

Conduct the gastric lavage and administer activated charcoal (four tablespoons 500 ml of water). Treat excitation or convulsions with the barbituate".

For use as an alpha adrenergic blocking agent Yocon (T.M.) is to be administered to an adult one tablet up to 3 times daily or as directed by a physician. The tablets are white uncoated spherical tablets containing yohimbine hydrochloride 5.4 mg (1/12 grain), bottled in 100 or 1000.

The article entitled "Effect of Yohimbine Hydrochloride on Erectile Impotence: A Double-Blind Study" provides in the abstract that the 34% response by patients taking yohimbine hydrochloride on erectile dysfunction was encouraging.

By way of tests, Applicant has administered such a tablet (described above) of 1/12 grain (5.4 mg) of yohimbine hydrochloride to patients who snored when they slept prior to bedtime (e.g. one half hour). The partners of the patients did not detect any snoring through the night.

As many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. An improved treatment for a person who snores, the treatment comprises the administration prior to sleep to the patient of an effective amount of yohimbine or any pharmaceutically tolerable form thereof in a pharmaceutically tolerable carrier to inhibit snoring in persons who snore.

2. The treatment of claim 1, wherein the effective amount of yohimbine comprises a tablet of (1/12 grain) 5.4 mg of yohimbine hydrochloride.

* * * * *